United States Patent [19]

Frabetti, Jr.

[11] 4,041,085

[45] Aug. 9, 1977

[54] ORTHO-ALKYLATION OF PHENOLS

[75] Inventor: Alton J. Frabetti, Jr., Wrentham, Mass.

[73] Assignee: General Electric Company, Pittsfield, Mass.

[21] Appl. No.: 632,561

[22] Filed: Nov. 17, 1975

Related U.S. Application Data

[63] Continuation of Ser. No. 852,453, Aug. 22, 1969, abandoned.

[51] Int. Cl.$^2$ .............................................. C07C 37/16
[52] U.S. Cl. ................................ 260/621 R; 260/620; 260/624 R; 260/624 C
[58] Field of Search ............... 260/620, 621 R, 624 C, 260/619 R, 624 R

[56] References Cited

U.S. PATENT DOCUMENTS

| | | | |
|---|---|---|---|
| 3,006,866 | 10/1961 | Corte et al. | 260/624 C |
| 3,446,856 | 5/1969 | Hamilton | 260/621 R |

FOREIGN PATENT DOCUMENTS

| | | | |
|---|---|---|---|
| 4968/69 | 2/1969 | Japan | 260/621 R |
| 717,588 | 10/1954 | United Kingdom | 260/621 R |

*Primary Examiner*—Norman Morgenstern
*Attorney, Agent, or Firm*—William F. Mufatti; Granville M. Pine; Edward A. Hedman

[57] ABSTRACT

This invention is for a process for the ortho-alkalation of phenols in the presence of a magnesium oxide alkylation catalyst. The process comprises the vapor phase reaction of a non-ortho-substituted phenol with an alcohol in the presence of an alkylation catalyst and is characterized by the introduction of water vapor into the reaction system. The water vapor effects continuous regeneration thereby substantially increasing catalyst life before regeneration is required. This is an important advantage as it increases the period of reactor operation before shut down is required, thereby making the overall process more economical.

12 Claims, No Drawings

ORTHO-ALKYLATION OF PHENOLS

This is a continuation of application Ser. No. 852,453 filed Aug. 22, 1969 now abandoned.

BACKGROUND OF THE INVENTION

1. Introduction

This invention relates to the ortho-alkylation of phenols and more particularly, to the vapor phase ortho-alkylation of phenols by reaction of a non-ortho-alkylated phenol with an alcohol in the presence of a magnesium oxide alkylation catalyst.

2. Description of the Prior Art

In commonly-assigned Hamilton U.S. Pat. No. 3,446,856 there is disclosed and claimed a method for methylating the ortho positions of phenol by the vapor phase reaction of a phenol with methanol in presence of magnesium oxide : a catalyst bed temperature in the range of 475° to 600° C. Under the conditions described in the Hamilton application, phenol is selectively ortho-methylated in yields of 95%. Thus, the reaction provides means for economically converting phenol to ortho-cresol, a useful disinfectant and wood preservative and for converting both phenol and ortho-cresol to 2,6-xylenol, a monomer which can be polymerized to form poly-2,6-xylenol, a high performance thermoplastic material.

While the Hamilton invention provides an economic synthesis for both 2,6-xylenol and ortho-cresol from phenol, the service life of the magnesium oxide catalyst is relatively short due to the high temperature at which the reaction is required to take place-i.e., about 40 to 60 hours service life at the typical temperature of about 530° C. After this period of time, catalyst must be regenerated before it can be re-used. Regeneration is a costly procedure as it involves shutting down the reactor, passing inert gases containing oxygen through the reactor, and gradually increasing the oxygen content in the inert gases until approximately 16 to 20% oxygen is contained in the gas stream.

In addition to the above difficulties, the magnesium oxide catalyst of the Hamilton patent is only moderately strong and frequent regenerations cause pellets of the catalyst to fragment. In addition, the use of modified magnesium oxide in powder form or in the form of a weakly sintered composite results in a relatively large induction period of maximum selectively. The term "induction period" may be defined as the period commencing with the start-up of the reaction to the time at which the catalyst reaches and maintains maximum ortho-alkylation selectively. Obviously, with a long induction period and a short catalyst life, the overall process becomes more costly.

Many of the above-noted difficulties are overcome by the processes of abandoned Van Sorge U.S. Pat. application Ser. Nos. 717,919 filed Apr. 1, 1968, 846,925 and abandoned application 846,973, now abandoned application 846,967; and, incorporated herein by reference. In these applications, processes are disclosed for the ortho-alkylation of phenol comprising the reaction of a non-ortho-substituted phenol with an alcohol in the presence of a modified magnesium catalyst comprising magnesium oxide having an inert binder such as a polymeric biner, silica and manganese oxide. In all of the above applications, one of the improvements is increased service life of the catalyst. However, even with the improvement in service life afforded by the inventions of the above applications, it is desirable to further increase the service life of the catalyst to decrease the overall cost of the process.

STATEMENT OF THE INVENTION

The present invention provides a process for the ortho-alkylation of phenols where catalyst service life is at least doubled using the magnesium oxide catalyst of the Hamilton patent or the modified magnesium oxide catalyst of the Van Sorge applications. The process comprises the vapor phase reaction of a non-ortho-substituted phenol with an alcohol in the presence of the alkylation catalyst and is characterized by the introduction of water vapor into the reaction system so that the alkylation reaction takes place in the presence of the water vapor. The reason for increased catalyst life is not fully understood, but is believed to be associated with a decrease in coking on the catalyst surface in the presence of water vapor.

DESCRIPTION OF THE PREFERRED EMBODIMENTS

The method for forming ortho-alkylated phenols according to the invention comprises vapor phase reaction of an alkyl alcohol and a non-ortho-substituted phenol in the presence of an alkylation catalyst at a temperature of at least 440° C, and preferably at a temperature varying between 460° C and 500° C. In general, the process is similar to the processes disclosed in the above-noted patent and copending applications and differs therefrom primarily in the addition of water vapor to the reaction system. The quantity of water vapor may be from 1 to 35% of the reactants, but is preferably maintained low, 3 to 15% by weight of the reactants being preferred.

While the invention has been described as applying specifically to phenols and ortho-cresol, it applies in general to phenols having an ortho-hydrogen. For example, it also applies to ortho-methyl phenol, ortho-ethyl phenol, and to phenols in which there are alkyl and aryl groups in the meta- and para-positions. These phenols may be represented by the formula:

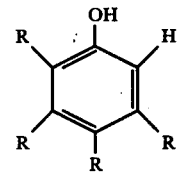

where each R is a monovalent substituent selected from the group consisting of hydrogen, alkyl, phenyl and alkyl-substituted phenyl.

In carrying our the alkylation in accordance with this invention, any one or a mixture of phenols having an ortho-hydrogen may be vaporized with alcohol and water and passed through a reactor heated to a temperature of at least 440° C containing the magnesium oxide catalyst. In order to obtain the maximum yield of ortho-alkylated products, at least one mole of the alcohol and preferably from 1 to 3 moles of the alcohol are used for each ortho-position on the phenol to be alkylated. For example, if phenol which has 2-ortho-hydrogens per molecule is to be methylated to produce a maximum yield of 2,6-xylenol, it is desirable to use two to six moles of methanol for each mole of phenol, with higher yields and selectivities being obtained with the higher ratio of methanol to phenol.

The vapors issuing from the reactor are condensed and the product separated by conventional methods such as crystallization, distillation, etc. The reaction proceeds at atmospheric pressure, but it is obvious that pressures above or below may be used.

The alkylation catalyst may be pure magnesium oxide in powder or loosely sintered form as disclosed in the Hamilton Patent or the modified magnesium oxide catalyst as disclosed in the copending Van Sorge applications. The modified magnesium oxide catalyst may be formed by blending finely divided magnesium oxide powders with finely divided powders of a binder such as manganese oxide, silica or an inert organic polymer. Preferably, both the powders of the magnesium oxide and the binder are of small particle size, an average particle size of less than 500 microns in diameter being preferred.

The percentage of binder in the catalyst blend is preferably maintained low and may be as low as 2% by weight on a dry solids basis or as high as 15% or more. The preferred range varies from 3 to 6% by weight. After the powders are blended, water is added to the blend in an amount sufficient to completely wet the blend so that it may be molded to shape. Typically, one part by weight water is added for each part of the powder blend. The blend is then molded to shape under light pressure, dried at about 200° F and subsequently calcined at an elevated temperature. A calcination temperature of between 400° and 500° F for a time up to about three hours is usually sufficient, but temperatures as high as 850° F may be used. As water is evaporated from the catalyst, minute pores form, thereby exposing the magnesium oxide and making the catalyst active. A surface area of at least 20, and preferably 120 to 200 square meters per gram of catalyst is desirable. The shape of the catalyst may be in the form of Raschig rings, cylinders, pellets, tablets or any other shape known in the art of heterogeneous catalysis.

The magnesium oxide used as a catalyst alone or in conjunction with a binder is a material having a very high surface to weight ratio. Magnesium oxide having the desired porosity may be prepared by thermally decomposing magnesium carbonate, basic magnesium carbonate or magnesium hydroxide as these materials may be converted to magnesium oxide without fusing or sintering.

Where manganese oxide is used as a binder, it is preferably prepared by precipitating the manganese oxide from an aqueous solution of manganese sulphate by mixing with an alkali such as potassium hydroxide. The precipitated manganese oxide powders are washed with pure or slightly alkaline water until substantially free of sulphate and alkali ions.

As indicated above, the process of this invention involving the introduction of water vapor into the reaction system substantially increased useful catalyst life before regeneration of the catalyst is required. In this respect, using pure sintered magnesium oxide, catalyst life is extended from a period of about 40 to 60 hours to a period of from 90 to 100 hours or more. Similar results are obtained with the modified magnesium oxide catalyst described in the above noted copending Van Sorge patent applications In the following examples, the system used consisted of a reservoir containing a solution of methanol, phenol and water, where applicable. The reservoir was connected to a metering pump which fed the reactants through a ¼ inch stainless steel tube into a vertical vaporizer made from a 12 inch long piece of 1 inch O.D., 0.8 inch I.D. stainless steel tubing. The vaporizer was partially immersed in a bath of fused salt to a depth of about 6 inch. The vapors from the reactor were fed to a 0.8 inch I.D. stainless steel tube reactor through a 1 inch length of ¼ inch I.D. stainless steel pipe located 5½ inch above the bottom of the vaporizer and connected to the reactor 13 inch from its bottom. The reactor was 24 inch long and was immersed in the fused salt bath to a depth of about 14 inch. Since the inlet tube of the reactor coming from the vaporizer also passed through the fused salt bath, it served as a heater for the vapor issuing from the vaporizer to bring the vapor up to the temperature of the reactor. The reactor was equipped with a thermo-well made from inch stainless steel tubing concentrically located in the reactor and extending downward into the catalyst bed to a depth of 1 to 6 inch. Thus, the catalyst bed temperature could be measured throughout a large section of the tube. The reactor tube was filled with a constant volume of 100 milliliters of catalyst which filled the tube to a depth of 12 inch. Thus, vapors were fed to the top of the catalyst bed in the reactor and product vapors left the reactor through a ⅜ inch I.D. stainless steel tube connected to the bottom of the reactor. The product vapors from the reactor were fed to a water cooled condenser-receiver.

EXAMPLES 1 and 2

The catalyst used in these examples were prepared by pelletizing and calcining substantially pure powders of magnesium oxide at a temperature of about 500° F. In Example 1, the reaction was performed in the absence of water. For comparison purposes, in Example 2, 10% water by weight of total reactants (phenol and alcohol) was fed with the methanol and phenol into the reaction system. The results are as set forth in the following table:

TABLE I

|  | Example 1 | Example 2 |
|---|---|---|
| Feed Composition |  |  |
| Molar ratio Methanol to Phenol | 6:1 | 6:1 |
| Wt. % water to feed | 0 | 10.0 |
| Operating Conditions |  |  |
| Temperature (° C.) | 510 | 504 |
| LHSV (hr.-1) | 1.83 | 1.65 |
| Pressure (psig) | 0 | 0 |
| Results |  |  |
| Induction Periods (hrs.) | 24 | 23.5 |
| Molar Phenol Selectivity (1) | 93.7 | 89.5 |
| Molar Methanol Selectivity (2) | 72.5 | 59.5 |
| Production Rate (lbs. 2, 6-xylenol/hr/cuft catalyst) | 19.3 | 14.0 |
| Catalyst Life (3) | 42.0 | 80.0 |

(1) The molar phenol selectivity is defined as the ratio of phenol converted to 2,6-xylenol to phenol converted to 2,6-xylenol and by-products multiplied by 100. The amount of phenol converted to orthocresol is not included in the definition as it is recycled in the feed stream if desired.
(2) The molar methanol selectivity is defined as the ratio of methanol reacted to form 2,6-xylenol to the methanol reacted to form 2,6-xylenol and by-products multiplied by 100. The amount of methanol converted to ortho-cresol is not included in the definition as it is recycled in the feed stream if desired.
(3) The catalyst life is defined as the time during which the production rate drops to 50% of the initial production.

As can be seen from the above table, the life of the catalyst of Example 1 was found to be 42.0 hours while that of Example 2 was found to be 80 hours, an increase of almost 100%.

EXAMPLES 3 and 4

The procedures of Examples 1 and 2 were repeated substituting a catalyst comprising magnesium oxide bonded with silica for the sintered pure magnesium oxide catalyst. The catalyst was prepared by blending 200 grams of commercial magnesium oxide with about 6 grams of silica powder, and about 200 grams of water. The blend was molded into cylindrically shaped pellets having a diameter and length of 3/16 inches. The catalyst was dried at 200° F and calcined by heating to about 850° F for about 3 hours. The catalyst was then placed in a reaction chamber which was maintained at a temperature of about 480° C. The conditions and results are set forth in the following table:

TABLE II

|  | Example 3 | Example 4 |
|---|---|---|
| Feed Composition |  |  |
| Molar Ratio Methanol to Phenol | 5:1 | 5:1 |
| Wt. % water to feed | 0 | 10 |
| Operating Conditions |  |  |
| Temperature (° C.) | 478 | 478 |
| LHSV (hr.-1) | 1.44 | 1.44 |
| Pressure (psig) | 0 | 0 |
| Results |  |  |
| Molar Phenol Selectivity | 94.0 | 92.0 |
| Molar Methanol Selectivity | 84.2 | 85.4 |
| Production Rate (lbs. 2, 6-xylenol/hr./ft. catalyst) | 24.1 | 22.1 |
| Catalyst Life | 220 hours | 400 hours |

From the above table, it can be seen that catalyst life is substantially increased using water in the reaction mixture.

EXAMPLE 5

Repetition of Example 4 with a decrease in the percentage of water contained in the feed fed to the reactor to 6.0% provides similar results with slightly greater phenol and methanol selectively and a catalyst life of approximately 380 hours.

While the foregoing discloses certain specific embodiments of the invention, it is understood that there are many modifications which obviously fall within the proper scope of the invention. Accordingly, the invention is to be limited in scope only as may be necessitated by the scope of the appended claims.

I claim:

1. In a process for selectively alkylating a phenol in the ortho position which comprises the vapor phase reaction in the presence of a magnesium oxide alkylation catalyst of an alkyl alcohol and a phenol having the general formula:

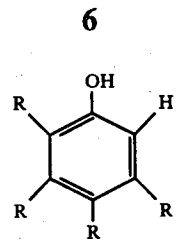

where R is a monovalent substituent from the group consisting of hydrogen, alkyl, phenyl and alkyl substituted phenyl; the improvement comprising adding water vapor to the vapor phase reaction in which said phenol is treated with said alkyl alcohol.

2. The process of claim 1 where the water vapor constitutes from 3 to 15% by weight of the alkyl alcohol and the phenol.

3. The process of claim 2 where the alcohol is methyl alcohol.

4. The process of claim 2 where the catalyst bed temperature is maintained at a temperature of at least 440° C.

5. The process of claim 2 where each R is a hydrogen.

6. The process of claim 2 where the phenol is ortho-cresol.

7. The process of claim 2 where the phenol is a mixture of unsubstituted phenol and ortho cresol.

8. The process of claim 2 where the magnesium oxide catalyst is substantially pure magnesium oxide.

9. The process of claim 2 where the magnesium oxide catalyst comprises magnesium oxide and from 2 to 15% by weight of a binder.

10. The process of claim 9 where the the binder is selected from the group consisting of silica, manganese oxides and organic polymeric binders.

11. The process of claim 10 where the organic polymeric binder is a cellulosic polymer.

12. In a process for selectively alkylating a phenol in the ortho position which comprises the vapor phase reaction in the presence of an alkylation catalyst comprising magnesium oxide and from 2 to 15% by weight of a binder which is a mixture of manganese oxides of an alkyl alcohol and a phenol having the general formula:

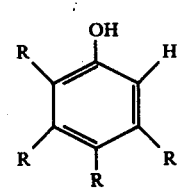

where R is a monovalent substituent from the group consisting of hydrogen, alkyl, phenyl and alkyl substituted phenyl, the improvement comprising adding from 3 to 15% by weight of water vapor based on the alkyl alcohol and the phenol to the vapor phase reaction in which said phenol is treated with said alkyl alcohol.

* * * * *

UNITED STATES PATENT AND TRADEMARK OFFICE
CERTIFICATE OF CORRECTION

PATENT NO. : 4,041,085
DATED : August 9, 1977
INVENTOR(S) : Alton J. Frabetti, Jr.

It is certified that error appears in the above-identified patent and that said Letters Patent are hereby corrected as shown below:

In Col. 1, line 18, after "oxide" and before "a", insert -- at --; on line 64, "biner" should read -- binder --.

In Col. 3, line 56, "increased" should read -- increases --.

In Col. 4, line 15, after "from" and before "inch", insert -- 1/8 --; on line 29, "were" should read -- was --.

Signed and Sealed this

Twentieth Day of December 1977

[SEAL]

Attest:

RUTH C. MASON
*Attesting Officer*

LUTRELLE F. PARKER
*Acting Commissioner of Patents and Trademarks*